United States Patent [19]

Fujimiya et al.

[11] Patent Number: 5,213,673
[45] Date of Patent: May 25, 1993

[54] MULTI-COLORED ELECTROPHORESIS PATTERN READING APPARATUS

[75] Inventors: Hitoshi Fujimiya; Hisanori Nasu, both of Yokohama, Japan

[73] Assignee: Hitachi Software Engineering Co., Ltd., Tokyo, Japan

[21] Appl. No.: 800,847

[22] Filed: Nov. 29, 1991

[30] Foreign Application Priority Data

Nov. 30, 1990 [JP] Japan .................................. 2-335554

[51] Int. Cl.$^5$ ............................................. G01N 27/26
[52] U.S. Cl. ............................ 204/299 R; 204/182.9; 356/344
[58] Field of Search ....................... 204/299 R, 182.8; 356/344, 417; 250/461.1, 461.2, 458.1

[56] References Cited

U.S. PATENT DOCUMENTS 4,657,095 7/1987 Kambara et al. ............... 204/299 R
4,833,332 5/1989 Robertson et al. .................. 356/417

FOREIGN PATENT DOCUMENTS 252683 1/1988 European Pat. Off. .
2203255 1/1989 Japan .................................. 356/344

Primary Examiner—John Niebling
Assistant Examiner—John S. Starsiak, Jr.
Attorney, Agent, or Firm—Fay, Sharpe, Beall, Fagan, Minnich & McKee

[57] ABSTRACT

A multi-colored electrophoresis pattern reading apparatus is capable of labelling each of plural samples separately with each of plural fluorescent substances having different fluorescence wavelengths, by electrophoresing the plural samples to develop a pattern, exciting the fluorescent substances labelled on the samples to emit fluorescence, and reading a fluorescent pattern emitting the fluorescence. The apparatus contains a source for the light for exciting the fluorescent substances; a light scanning mechanism for scanning the light to irradiate a gel in the direction of its thickness with the light; a light receiving section for receiving fluorescence resulting from the light source separated from the scattered light resulting from a reading surface on the basis of a spatial position relationship of a light receiving path by setting a light receiving surface in a direction different from an optical axis of the irradiating light; an optical filter section for separating the resulting optical signals section into plural wavelengths; an optoelectric conversion section for converting optical signals into electrical signals; and an amplifier for amplifying the electrical signals by an integrating operation corresponding to scanning of the irradiating light, and for generating electrical signals indicative of fluorescence from the pattern one after another.

8 Claims, 11 Drawing Sheets

C/D CONTROL SIGNAL

MULTI-COLORED ELECTROPHORESIS PATTERN READING APPARATUS

BACKGROUND OF THE INVENTION

The present invention relates to a multi-colored electrophoresis pattern reading apparatus and, more particularly, to a multi-colored electrophoresis pattern reading apparatus appropriate for the comparison of a plurality of electrophoresis patterns by labelling each of a popularity of samples with fluorescent pigments having different fluorescent wavelengths simultaneously, subjecting the samples to electrophoresis other, and reading the resulting electrophoresis pattern.

Generally, electrophoresis analysis methods using labels with a radioactive isotope have been employed for analyzing the sequence of various genes, including diagnosis of diseases deriving from genes, the structures of proteins such as amino acids, etc. The electrophoresis analysis method is a method for analyzing samples by labelling or replacing fragments of a sample with or by a radioactive isotope, subjecting the fragments of the sample to electrophoresis with a gel, and analyzing a pattern of distribution of the fragments of the sample developed by means of electrophoresis.

Description will now be made of the diagnosis of hereditary diseases as an exemplary application for reading and analyzing the electrophoresis patterns. The human genome DNA consists of pairs of bases numbering approximately $3 \times 10^9$ and the sequence of the bases is generally constant among all human beings, although there is a deviation in the sequence of the bases for certain individuals. This deviation is called a polymorphism of DNAs. The polymorphism of DNAs is seen in the non-hereditary region as well as in the hereditary region, and the polymorphism of DNAs appears in many occasions as a polymorphism of proteins, that is a phenotype of the polymorphism of DNAs. Many variations seen among human beings, such as blood types, histocompatible antigens, the difference of skin and hair colors among peoples, etc. are based on the polymorphism of DNAs. The polymorphism of the DNAs has been created on the basis of variations that have been accumulated in the DNAs of the genocytes of the human groups up to the present time from the time when the human being developed as an individual biological species in the course of evolution. When such a variation exists in the site that has the function of significance in terms of the existence as an individual person, and when a nosogenic phenotype resulting from the variation occurs as a pathologic state, the pathologic state is called a hereditary disease. It is said that there are currently more than 3,000 kinds of hereditary diseases in the human group.

The nosogenesis of the hereditary disease is an abnormality appearing on the DNA sequence. However, it is recognized for the first time as a disease in several stages ranging from DNA through mRNA and proteins to pathogenic phenotype., The diagnosis as a disease is conducted usually in the last stage and the diagnosis can be implemented at the DNA level or at the protein level if the disease would occur simply in the course of the several stages as described hereinabove.

The basic technique for the diagnosis of DNAs is called Southern plotting that basically consists of six steps Step 1: Extraction of DNAs as a sample;
Step 2: Fragmentation of DNAs with restricting enzymes;
Step 3: Fractionation of molecular weights of the DNAs through gel electrophoresis;
Step 4: Migration of DNA fractions to filter;
Step 5: Hybridization of DNA fractions with probe DNA (obtained by labelling DNA having the homeomorphous sequence of the gene to be detected); and
Step 6: Detection of the hybrid by autoradiography.

For the diagnosis of the hereditary diseases, DNAs extracted from any organ are employed, and the sample required for that purpose is usually the peripheral blood of the order of several milliliters. DNAs are extracted from the leukocytes separated from the peripheral blood as the sample. Approximately five days are usually required from step 1 to step 6. In diagnosing the hereditary diseases, a fraction pattern of a person tested is compared with a fraction pattern of a normal person. The person tested is decided as normal when the fraction pattern of the person tested is determined to be identical to the fraction pattern of the normal person.

Recently, attempts have been made to conduct tests by using a probe DNA labelled with a fluorescent pigment, in place of a radioactive isotope, exciting the fluorescent pigment and reading the electrophoresis pattern, from the point of view of safety and other environmental problems. However, highly sophisticated optical and signal processing techniques are required to give a signal-to-noise ratio equivalent to the radioactive isotope method, because the quantity of the sample required for diagnosis of the hereditary disease and determination of the sequence of bases is of the order of approximately $10^{-15}$ mole.

Japanese Patent Laid-open Publication (kokai) No. 61-62,843/1986 discloses an electrophoresis apparatus capable of detecting a minute quantity of a sample labelled with a fluorescent pigment.

Description will now be made of such an electrophoresis apparatus based on a fluorescence detection method.

FIG. 16 is a perspective view showing an appearance of a conventional electrophoresis apparatus of a fluorescent type. The electrophoresis apparatus comprises an electrophoresis and instrumentation unit 51 for implementing electrophoresis of a sample and measuring the distribution of fluorescence, data processor 52 for performing data processing on the basis of measured data, and a cable 53 connecting the electrophoresis and instrumentation unit 51 to the data processor 52. The electrophoresis and instrumentation unit 51 has a door 51a through which are poured a gel serving as a base for performing electrophoresis for DNA fragments and a predetermined quantity of a sample for electrophoresis. As the door 51a is closed a switch for starting electrophoresis on an operation display panel 51b is pressed to start electrophoresis. After the electrophoresis has been started, a monitor of the operation display panel 51b of the electrophoresis and instrumentation unit 51 displays an operational state. The data measured is transmitted to the data processor 52 in which the data is processed on the basis of a predetermined program stored in advance. The data processor 52 comprises a computer body 54, a keyboard 55 for entering an instruction from the operator, a display unit 56 for displaying the processing state and results, and a printer 57 for recording the processed results.

FIG. 17 is a block diagram showing the configuration of the inside of the electrophoresis and instrumentation unit. As shown in FIG. 17, an overall configuration of the electrophoresis and instrumentation unit 51 (FIG. 16) comprises an electrophoresis unit section 63 and a signal processor unit section 64. The electrophoresis unit section 63 comprises an electrophoresis section 5 for implementing electrophoresis, a first electrode 2a and a second electrode 2b each for applying voltage to the electrophoresis section 5, a support plate 3 for supporting the electrophoresis section 5 as well as the first and second electrodes 2a and 2b, a power plant unit 4 for applying voltage to the electrophoresis section 5, a light source 11 for emitting light for exciting a fluorescent substance, an optical fiber 12 for leading the light from the light source 11, a light collector 14 of an optic system for condensing and collecting fluorescence 13 generated by the fluorescent substance, an optical filter 15 for selectively passing light having a particular wavelength therethrough, and an optical sensor 16 for converting the condensed light into electric signals. The signal processor unit section 64 comprises an amplifier 17 for amplifying the electric signals from the optical sensor 16, an analog-digital converting circuit 18 for converting analog signals of the electric signals into digital data, a signal processing section 19 for pre-processing the digital data, for example, by performing addition average processing or the like, an interface 20 for implementing interface processing for feeding the pre-processed data to an external data processor, and a control circuit 10 for implementing overall control of the electrophoresis unit section and the signal processing system. The digital signal OUT generated from the signal processor unit section 64 is transmitted to the data processing unit 52 (FIG. 16), thereby implementing the data processing such as analysis processing and so on.

Description will now be made of the operation of the electrophoresis apparatus with reference to FIGS. 16 and 17.

After the door 51a of the electrophoresis and instrumentation unit 51 is opened, a gel is poured into the electrophoresis section 5 disposed within the electrophoresis and instrumentation unit 51 and thereafter a sample of DNA fragments labelled with a fluorescent substance is poured thereinto. After a switch of the instrument panel 51b is pressed to give an instruction to start electrophoresis, voltage is applied from the first and second electrodes 2a and 2b of the power plant unit 4 to the electrophoresis section 5, thereby starting the electrophoresis. The electrophoresis allows the sample labelled with the fluorescent substance to migrate, for example, in lanes 71, 72, 73 and 74, as shown in FIG. 20, gathering the molecules having the same molecular weights together form bands 66. The molecules having lower molecular weights migrate faster than those having higher molecular weights so that the former migrate a distance longer than the latter within the same time unit.

The bands 66 are detected in a manner as shown in FIG. 18a by leading light from the light source through the optical fiber 12 to a light path 61 and irradiating the gel on the light path 61 with the light, exciting the labelled fluorescent substance concentrated on the bands 66 in the gel to generate fluorescence 13, and detecting the fluorescence 13. The fluorescence 13 is generated form the fluorescent substance in concentration as low as approximately $10^{-16}$ mole per band, although the quantity of fluorescence may depend upon an absorptivity, or extinction coefficient, of the fluorescent substance used, quantum efficiency thereof, intensity of exciting light, etc. For instance, fluorescein isothiocyanate has a peak of wavelength of excitation at 490 nm, a peak of its fluorescent wavelength at 520 nm, an extinction coefficient of $7\times10^4$ mole$^{-1}$.cm$^{-1}$, and a quantum efficiency of approximately 0.65. If fluorescein isothiocyanate exists in the concentration of $10^{-16}$ mole per band, the fluorescence generated contains photons of the order of as low as $10^{10}/S$, when calculated by postulating the use of argon ion laser of a wavelength of 488 nm at an output of 1 mW as a fluorescent substance, although it may vary to some extent with the thickness of the gel or the like.

Referring to a front view as shown in FIG. 18a and to a longitudinally sectional view as shown in FIG. 18b, the electrophoresis section 5 comprises a gel member 5a composed of polyacrylamide or the like and gel supporting members 5b and 5c, each made of glass for supporting and interposing the gel member 5a from the both sides. A sample of DNA fragments is poured into the gel member 5a of the electrophoresis section 5 from its upper portion and the electrophoresis is carried out by applying electrophoresis voltage to the first electrode 2a and the second electrode 2b (FIG. 17).

While the electrophoresis is being carried out, the fluorescent substance contained in the bands of the electrophoresis pattern in the gel member 5a along the light path 61 is irradiated with rays of light sent out from the light source, such as laser light, which pass through the optical fiber 12 onto the light path 61 of the gel member 5e. This allows the fluorescent substance present on the light path 61 to be excited to emit fluorescence 13 that is led to a light collector 14 of optics consisting of a combination of lenses, and then selected by the optical filter 15 after having been condensed, followed by conversion into electrical signals by means of a one-dimensional optical sensor 16.

In order to convert a faint quantity of light into electrical signals in an efficient fashion, the light is amplified $10^4$ to $10^5$ times with an image intensifier or the like, and the image is converted into electrical signals by the optical sensor 16, such as a one-dimensional CCD optical sensor or the like. The electrical signals converted by the optical sensor 16 are then amplified to signals of a desired level by the amplifier 17, and the analog signals are converted into digital signals by the analog-digital converting circuit 18, followed by transmission to the signal processing section 19. The digital signals transmitted from the analog-digital converting circuit 18 are then subjected to signal processing, such as addition average processing, or the like, in order to improve the signal-to-noise ratio (an S/N ratio), and the resulting digital data are transmitted to the data processor unit section 52 through the interface 20.

FIGS. 19a and 19b are schematic representations for describing an example of signals of a pattern indicative of a fluorescent intensity of DNA fragments transmitted from the electrophoresis and instrumentation unit 51. For instance, as shown in FIG. 19a, the fluorescent substance present on the light path 61 is excited upon irradiation of the gel member 5a of the electrophoresis section 5 with the laser light in the course of electrophoresis, thereby emitting fluorescence. The fluorescence is detected at predetermined positions of each lane in the direction of electrophoresis, as indicated by 62, as the time of electrophoresis elapses. In other words, the fluorescence is detected as the bands 66 of each lane passes through the positions of the light path 61, thereby detecting a pattern signal of fluorescence intensity in each of the lanes, as shown in FIG. 19b. As a peak of the fluorescence intensity is given when each of the bands 66 passes through the position of the light path 61, the pattern signal of the fluorescence intensity as shown in FIG. 19b represents a pattern signal indicating the magnitude of fluorescence intensity of the bands 66 located in the direction of electrophoresis, as indicated by 62.

The computer body 54 of the data processing unit 52 implements data processing for comparing molecular weights and determining a sequence of bases of a DNA chain on the basis of data of the pattern indicative of fluorescence intensity in response to data of the pattern signals for the fluorescence intensity of the DNA fragments transmitted from the electrophoresis and instrumentation unit 51. The sequence of the bases and so on determined by the data processing is symbolized and then generated, thereby displaying the symbolized data on a display screen by the display unit 56 or printing it out by the printer 57.

The aforesaid embodiment is directed to an example of the apparatus in which the fluorescent pigment is employed for labelling the sample. Japanese Patent Laid-open Publication (kokai) No. 1-167,649/1989 discloses another example of an apparatus capable of reading a fluorescent electrophoresis pattern. This apparatus reads a fluorescent pattern of the electrophoresis section as a whole after the end of electrophoresis, unlike the aforesaid electrophoresis apparatus, which reads the distribution of the fluorescent pattern passing through a reading section in the course of electrophoresis.

It is to be noted herein that the gel electrophoresis method employed for the electrophoresis pattern reading apparatuses on the basis of the fluorescence detection method is the same as the gel electrophoresis method which has been employed for the conventional apparatuses in which the sample is labeled with the radioactive isotope. The gel electrophoresis method may cause a warp in the electrophoresis pattern because the speed of migration of bands may vary with the position of an electrophoresing plate due to irregularities in temperatures within the gel and for other reasons, thereby causing a warp in the electrophoresis pattern. Hence, for example, when electrophoresis of two kinds of samples or two dimensional electrophoresis is to be performed to compare two kinds of electrophoresis patterns for the diagnosis of hereditary diseases, the electrophoresis positions may be deviated between the electrophoresis results due to the warp and a comparison between the two electrophoresis patterns may be rendered difficult, regardless of the method adopted, as long as the conventional gel electrophoresis method is employed. Further, implementation of the correction of such electrophoresis patterns by means of data processing is also rendered laborious and difficult.

Further, as the electrophoresis and instrumentation unit for implementing electrophoresis and simultaneously measuring the distribution of the fluorescent substance passing through the reading unit adopts two-dimensional electrophoresis, it requires the one-dimensional electrophoresis to be implemented by one device and the two-dimensional electrophoresis to be conducted by another device, so that this operation is laborious.

SUMMARY OF THE INVENTION

The object of the present invention is to provide a multi-colored electrophoresis pattern reading apparatus suitable for a comparison between a plurality of electrophoresis patterns by labelling each of plural samples with a fluorescent pigment having a different fluorescence wavelength, subjecting the samples to electrophoresis simultaneously, and reading the resulting electrophoresis patterns.

Another object of the present invention is to provide a multi-colored electrophoresis pattern reading apparatus capable of reading the fluorescent patterns of the electrophoresis patterns and comparing the electrophoresis patterns without warp resulting from the electrophoresis.

In order to achieve the aforesaid objects, the present invention consists of a multi-colored electrophoresis pattern reading apparatus capable of labelling each of plural samples separately with each of plural fluorescent substances having different fluorescence wavelengths. subjecting the plural samples to electrophoresis to develop an electrophoresis pattern, exciting the fluorescence. The invention 5 further substances labelled on the respective plural samples to emit fluorescence, and reading a fluorescent pattern emitting the fluorescence, characterized by a light source means for irradiating the electrophoresis pattern with irradiating light for exciting the fluorescent substance labelled on the sample; a light scanning means for scanning the irradiating light from the light source means and irradiating a gel in the direction of thickness of the gel with the irradiating light; a light receiving means for receiving the fluorescence resulting from the electrophoresis pattern by separating scattered light resulting from a reading surface on the basis of a spatial position relationship of a light receiving path by setting a light receiving surface in a direction different from an optical axis of irradiating light; an optical filter means for separating optical signals received by the light receiving means into plural fluorescence wavelengths; an optoelectric conversion means for generating electrical signals by subjecting the optical signals separated by the optical filter means to optoelectric conversion; and an amplifier means for amplifying the electrical signals from the optoelectric conversion means by an integrating operation corresponding to scanning of the irradiating light, and for generating electrical signals indicative of the fluorescence from the electrophoresis pattern one after another.

The light source means is a light source for generating irradiating light for emitting fluorescence by exciting two or more fluorescent substances labelled separately on the samples. In order to give light having wavelength for exciting each of the fluorescent substances, for example, a plurality of light sources may be provided to generate a mixture of light from the plurality of the light sources. The light source means may be a single light source when the light resulting from the single light source has a predetermined range of wavelengths.

The light scanning means is arranged to scan the irradiating light from the light source means and radiate in the direction of thickness of the gel. The light receiving means has its light receiving surface set in a different direction different from the optical axis of the irradiating light, and is designed so as to receive the fluorescence from the electrophoresis pattern separated from the scattered light from the reading surface due to the spatial position relationship of a light receiving path.

The optical filter means can separate the optical signals of the fluorescence received by the light receiving means into a plurality of fluorescence wavelengths. The optoelectric conversion means generates the electrical signals by optoelectrically converting each of the optical signals separated by the optical filter means, and the amplifier means amplifies very faint electrical signals by implementing an integrating operation corresponding to the scanning of the irradiating light, and by generating the electrical signals of fluorescence from the electrophoresis pattern one after another. The speed of the integrating operation is so arranged as to correspond to the speed at which the irradiating light is scanned, thereby allowing very faint fluorescence outputs to be amplified in an efficient way.

The multi-colored electrophoresis pattern reading apparatus having the configuration as described above can read the distribution of the fluorescent substances by the difference in wavelength of fluorescence inherent in the fluorescent pigments from the electrophoresis pattern of the samples. Further, the multi-colored electrophoresis pattern reading apparatus according to the present invention allows all the samples, including the comparative sample, to undergo an equal degree of warp due to electrophoresis, so that the electrophoresis results can be read without paying attention to the warp originating from electrophoresis.

Other objects, features and advantages of the present invention will become apparent in the course of the description of the preferred embodiments, which follows, with reference to the accompanying drawings.

DESCRIPTION OF THE PREFERRED EMBODIMENTS

Figure 1:
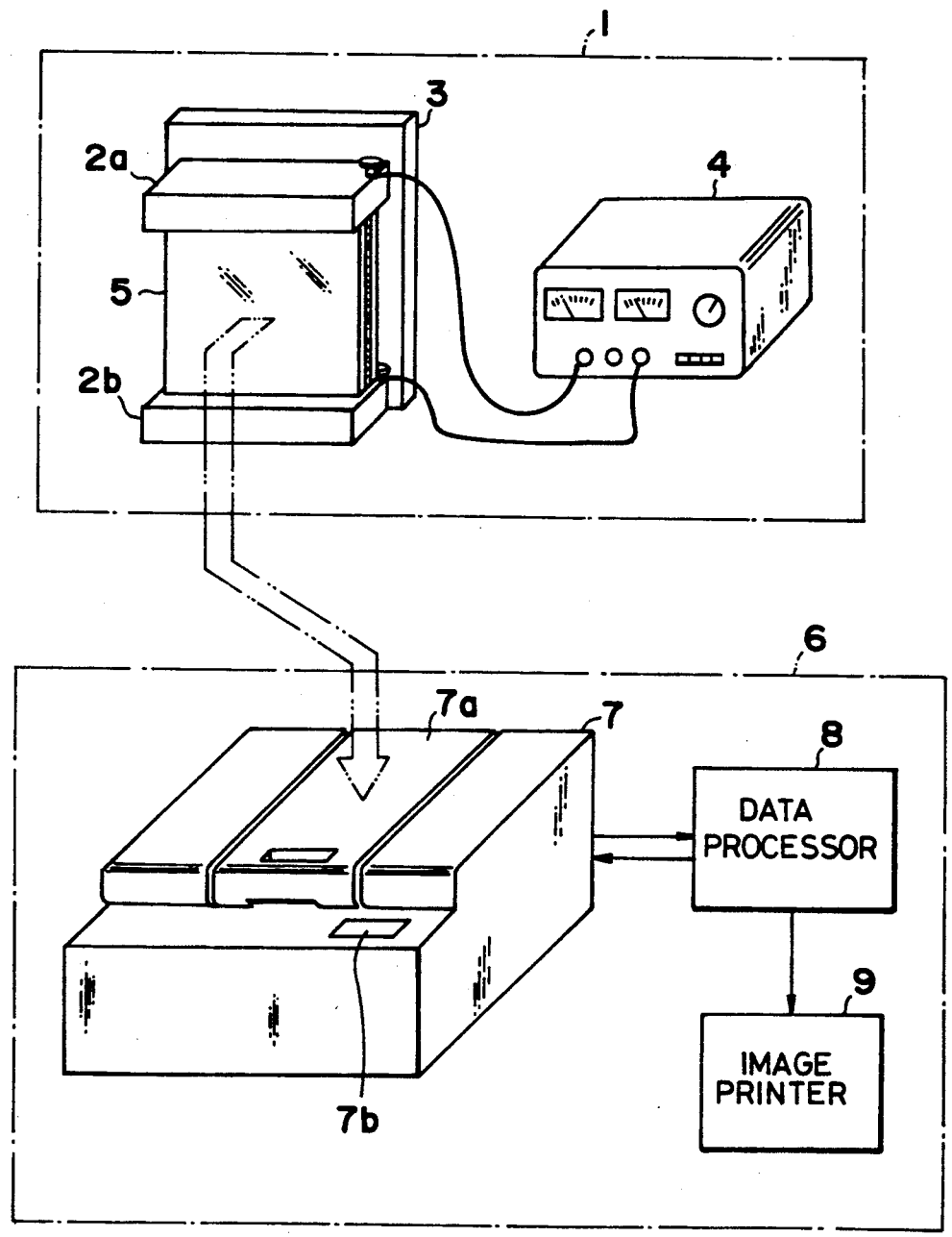
FIG. 1 is a schematic representation showing an overall configuration of the electrophoresis pattern reading apparatus of a fluorescent type according to an embodiment of the present invention.

FIG. 1 is a schematic representation showing an overall configuration of the electrophoresis pattern reading apparatus of a fluorescent type according to an embodiment of the present invention.

As shown in FIG. 1, the apparatus comprises a combination in which an electrophoresis, unit 1 is connected to a reading unit 6 disposed separately from the electrophoresis unit. The electrophoresis unit 1 comprises an electrophoresis unit section 5, a first electrode 2a, a second electrode 2b, a supporting plate member 3, and a power plant 4 for an electrophoresis. The electrophoresis unit section 5 consists of a gel member serving as a base for electrophoresis, and a gel support member for supporting the gel member, comprising opposed glass panels or the like for interposing the gel member, and it is mounted to the first and second electrodes 2a and 2b which in turn apply electrophoresis voltage to the electrophoresis unit section 5. The supporting plate member 3 is arranged to support the electrophoresis unit section 5 as well as the first and second electrodes 2a and 2b. The power plant 4 supplies the electrophoresis voltage.

Figure 18A:
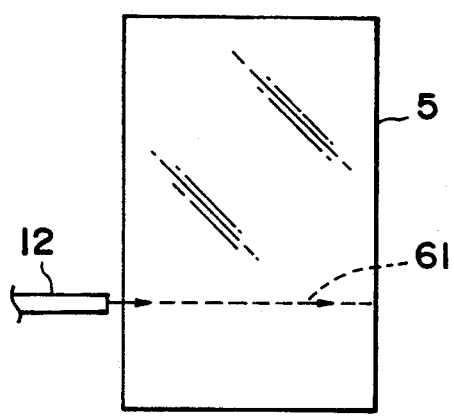
FIG. 18a and 18b are and elevational view and a longitudinally sectional view respectively showing the electrophoresis unit, in order to describe the principle of the operations for detecting the electrophoresis pattern by the fluorescence method.
Figure 18B:
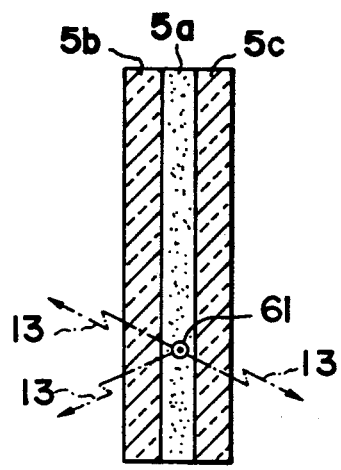
Figure 19A:
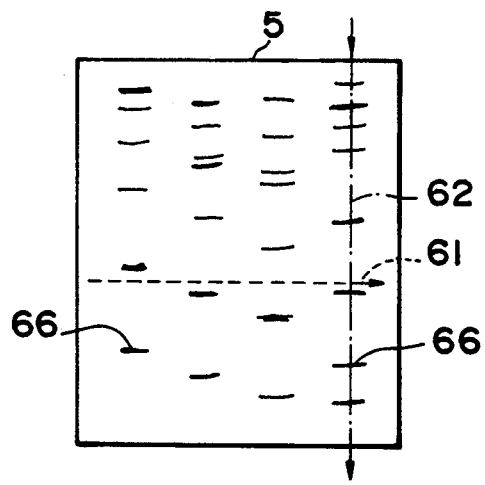
FIG. 19a is a schematic representation showing an example of a pattern of DNA fragments.
Figure 19B:
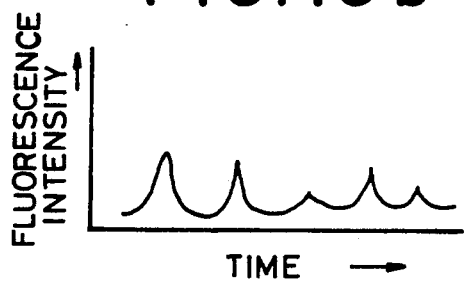
FIG. 19b is a graph showing an example of signals of a fluorescent intensity pattern of the DNA fragments to be generated from the electrophoresis and instrumentation unit.
Figure 20:
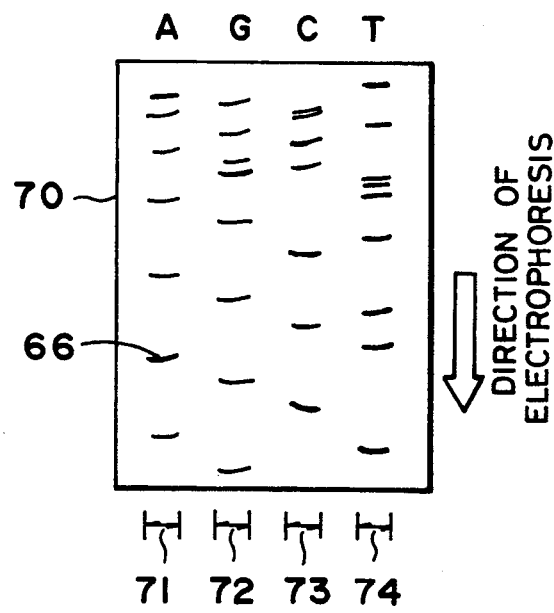
FIG. 20 is a schematic representation showing an example of distribution of DNA fragments that have been electrophoresed.

As described hereinabove, the electrophoresis unit section 5 is composed of the gel member for developing a sample for electrophoresis, such as polyacryl amide or the like, and the gel support member for supporting the gel member interposed from both sides by the glass plate panels or the like (see FIGS. 18a and 18b). A sample of DNA fragments to be electrophoresed is fed from an upper portion of the gel member of the electrophoresis unit section 5, and the electrophoresis voltage is applied to the first and second electrodes 5a and 5b from the power plant 4, thereby enabling electrophoresis of the sample to give an electrophoresis pattern. The electrophoresis unit section 5 is removed or detached from the electrophoresis unit 1 after electrophoresis has been finished and mounted to the reading unit 6 for reading the resulting electrophoresis pattern.

As the electrophoresis unit section 5 is mounted to an instrumentation unit body 7 of the reading unit in a state in which it is removed or detached from the electrophoresis unit 1 or in a state in which only the gel member is removed form the electrophoresis unit section 5, the resulting electrophoresis pattern is read and data are then processed by the reading unit 6. As shown in FIG. 1, the reading unit 6 has the instrumentation unit body 7 as an essential portion, and a data processor 8, an image printer 9 and other accessories are mounted to the instrumentation unit body 7.

The data processor 8 is arranged to implement data processing, image processing and determination processing for the data resulting form the electrophoresis pattern read by the instrumentation unit body 7. The image printer 9 to process and print the electrophoresis pattern data.

The instrumentation unit body 7 has a reading table disposed immediately below a lid 7a mounted at the upper portion of the instrumentation unit body for reading the electrophoresis pattern from the electrophoresis unit section 5 consisting of the gel member and the gel support member, wherein the electrophoresis is performed. After the electrophoresis unit section 5 is detached from the electrophoresis unit 1 after electrophoresis, the lid 7a disposed at the upper portion of the instrumentation unit body 7 is opened and the electrophoresis unit section 5 is then mounted to the reading table. After mounting the electrophoresis unit section 5 to the reading table, the lid 7a is closed and a start switch for starting the reading of the electrophoresis pattern on an operational display panel 7b of the instrumentation unit body 7 is pressed, thereby imitating the reading of the electrophoresis pattern.

As the reading of the electrophoresis pattern starts, the scanning of the irradiating light from a spot light source built in the instrumentation unit body 7 is started, and the gel member of the electrophoresis unit section 5 is irradiated with the light for exciting a fluorescent substance, thereby causing fluorescence. The fluorescence emitted upon irradiation with the light is received, and a pattern of distribution of the fluorescent substance is measured.

The data processor 8 then processes the data read and measured by the instrumentation unit body 7 and further controls the instrumentation unit body 7 itself. Finally the processed data is printed out by the image printer 9. In this embodiment, the image printer 9 is of a type capable of printing with a plurality of colors, thereby permitting the electrophoresis patterns to be printed out with multiple colors so as to correspond to the samples.

Figure 2:
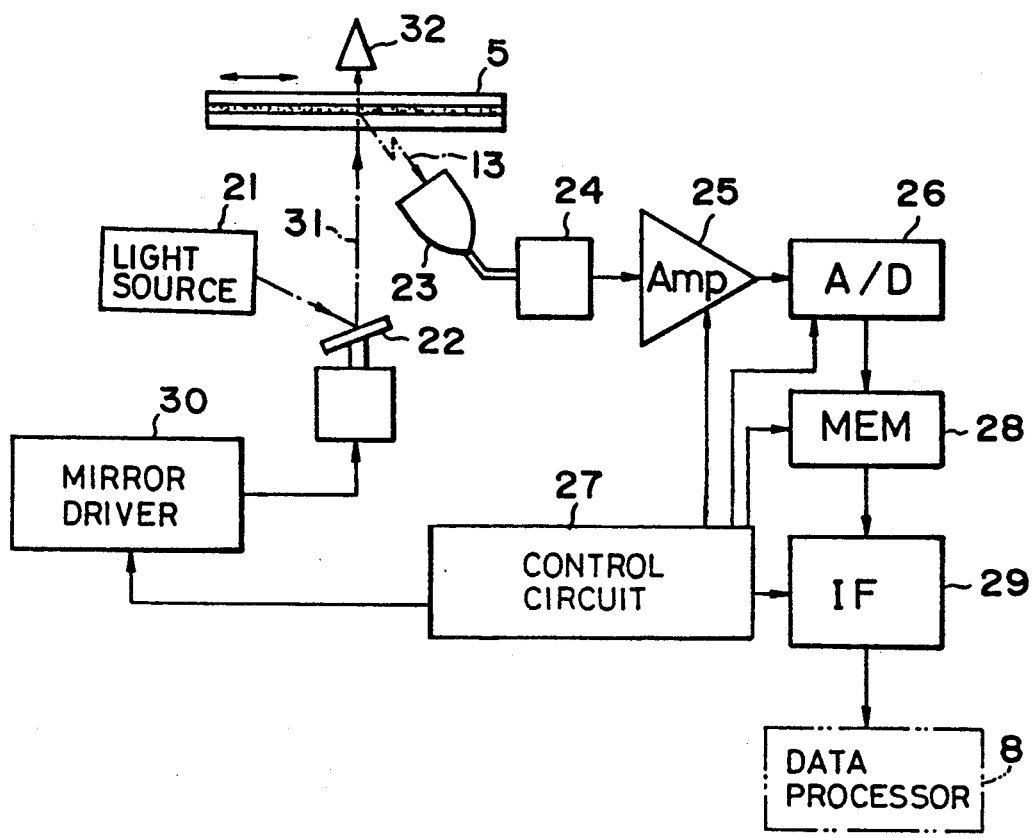
FIG. 2 is a block diagram showing the configuration of the essential portion of the instrumentation section body.
Figure 3:
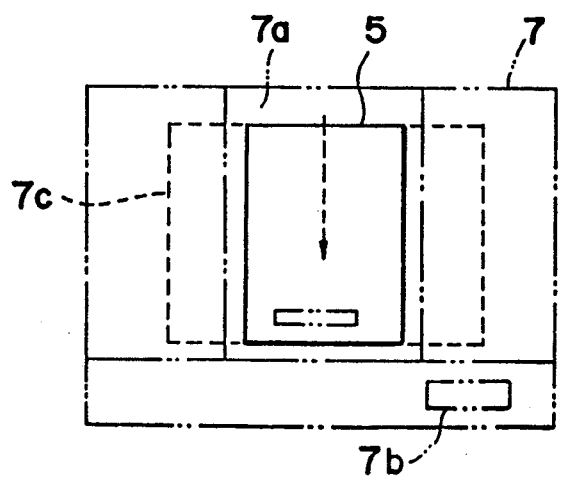
FIG. 3 is a view showing the position in which an electrophoresis unit is to be mounted to the instrumentation section body.

FIG. 2 is a block diagram showing the configuration of the essential portion of the instrumentation unit body 7, and FIG. 3 is a view showing the position in which an electrophoresis unit is to be mounted to the instrumentation section body 7.

In performing the analysis of each of plural samples by means of electrophoresis with the multi-colored electrophoresis pattern reading apparatus of fluorescent type, the samples of DNA fragments labelled with the fluorescent pigments or fluorescent substances are subjected to electrophoresis with the electrophoresis unit 1 for a predetermined period of time, for example, as long as approximately 5 hours. After the electrophoresis has been finished, the electrophoresis unit section 5 is detached from the electrophoresis unit 1 and the gel member of the electrophoresis unit section 5 removed therefrom is then mounted to an upper portion of the reading table 7c through the lid 7a of the instrumentation unit body 7 of the reading unit 6, as shown in FIG. 3, in such a state that the gel member is still interposed with the gel support member, such as glass plates, or that the gel support member is detached from the electrophoresis unit section 5. Then, the lid 7a is closed, thereby finishing the setting of the electrophoresis sample to the reading unit. When no gel member is yet labelled with the fluorescent pigment after electrophoresis, the gel member may be labelled therewith in this stage of mounting the electrophoresis pattern. The gel may be dried before mounting to the reading table.

Then, operations are performed for instructing the start of reading the electrophoresis pattern by pressing the read starting switch of the operation display panel 7b or by giving an instruction to start reading from the data processor 8. In starting the reading operations through the data processor 8, the state of mounting the electrophoresis unit section 5 to the instrumentation unit body 7 is transmitted through a control signal line to the data processor 8 which in turn controls the operations of the reading unit section of the instrumentation unit body 7 in accordance with the state of mounting the electrophoresis unit section 5. In this case, parameters such as reading speed and so on during operations may be set and registered in advance on the side of the data processor 8, thereby allowing the operations for starting the reading to be performed automatically, and reducing burden for operating the switches on the part of an operator.

The read data on the distribution of the fluorescent pigments are transmitted to the data processor 8 which in turn implements desired processing programmed in advance, such as processing for detecting a peak of the intensity of fluorescence, electrophoresis distance, and so on. The data of the processed results are printed out, when needed, by the image printer 9 as an image having a shade of color in accordance with the intensity of fluorescence or as image in an which the intensity of fluorescence is divided by contour lines, colors or concentrations of color. The image having the shade of color in accordance with the intensity of fluorescence looks equal to an X-ray film image of data obtained by labelling the sample with a radioactive isotope in the conventional manner, and subjecting the sample to electrophoresis. The data of the results after data processing may be stored, when needed, as digital data in a magnetic or optical recording device.

Referring to FIG. 2 showing the configuration of the instrumentation unit body 7, laser beams, as indicated by 31, emitted from the light source 21 are scanned in the direction from the front to the rear in the drawing with the vibrating mirror 22 to be driven by the mirror driver 30 and the gel member as an object of reading is exposed to the laser beams 31. The spot lights of the laser beams 31 scanned by the vibrating mirror 22 irradiate the gel member of the electrophoresis unit section 5 in the direction of thickness of the gel member thereof while moving. The gel member of the electrophoresis unit section 5 emits fluorescence upon irradiation with the spot lights of the scanned laser beams 31, and the resulting fluorescence, as indicated by 13, is received by the light collector 23.

The light collector 23 is arranged to have a light path for receiving fluorescence 13 having an optic axis so as to be deviated from the optic axis of the spot light thrown on the electrophoresis unit section 5, and the optical lens system is arranged in a spatial position relationship of the light path so as to receive the fluorescence, as indicated by 13, with enhanced sensitivity to separate the scattered light emitted from the irradiated surface of the electrophoresis unit section 5.

The light received by the light collector 23 is converted into electrical signals by the optoelectric conversion section 24 and then amplified by the amplifier 25. An optic trap 32 is mounted on the side opposite to the surface of the electrophoresis unit section 5 to be irradiated with the laser beams 31 in order for the laser beams 31, as stray light, to cause no adverse influence upon the surface of the electrophoresis unit section 5 after transmission through the gel member.

The light collector 23 receives the fluorescence 13 through the optoelectric conversion section 24 with enhanced sensitivity to the fluorescence 13 to be detected, and the fluorescence 13 is then converted through the optoelectric conversion section 24 into electrical signals which in turn are amplified by the amplifier 25 and entered into the analog-digital conversion circuit 26, whereby the electrical signals are converted into digital data. The signals detected from the fluorescence and converted into digital data are stored by the memory 28 and transmitted to the data processor 8 through the interface 29. The overall control over the signal processing is carried out by the control circuit 27.

Figure 4:
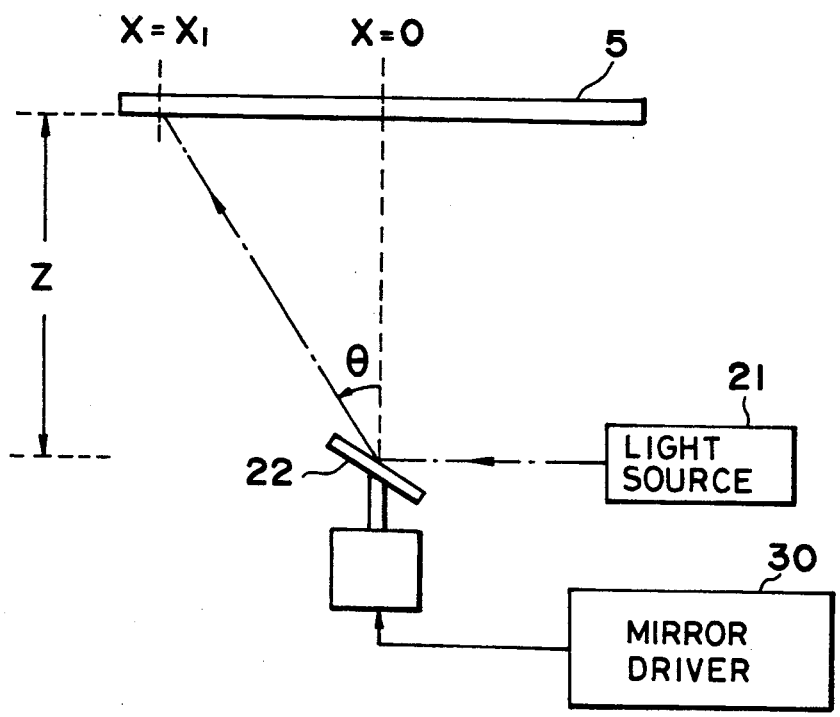
FIG. 4 is a view showing the light scanning mechanism for scanning a gel surface with laser beams by using a vibrating mirror.
Figure 5:
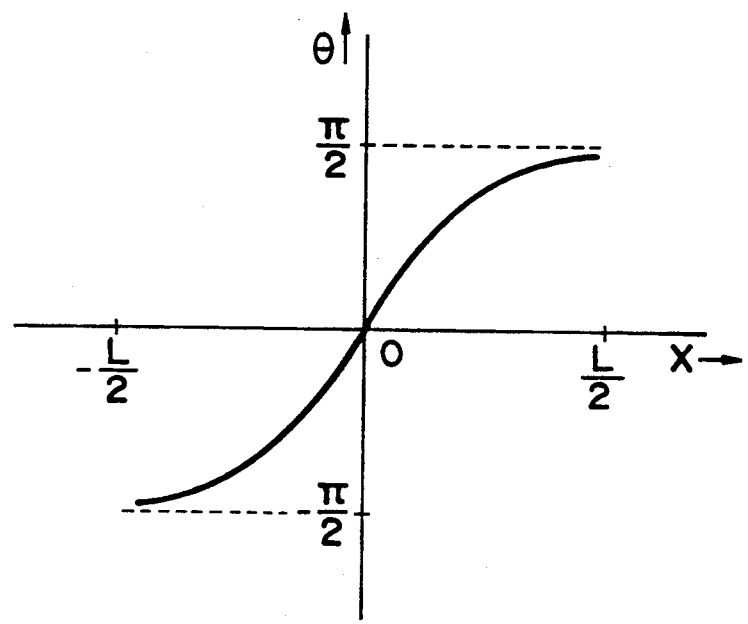
FIG. 5 is a graph showing the relationship between the angles of rotation of the vibrating mirror and the distance through which the spot light of the laser beams moves.

Description will now be made of the configuration of each portion of the instrumentation unit body of the electrophoresis pattern reading apparatus (as shown in FIG. 2). FIG. 4 is a view showing the light scanning mechanism for scanning a gel surface with laser beams by using the vibrating mirror, and FIG. 5 is a graph showing the relationship between the angles of rotation of the vibrating mirror and the distance in which the spot light of the laser beams moves.

Referring to FIG. 4, the light source 21 and the vibrating mirror 22 are disposed in the illustrated positions relative to the electrophoresis unit section 5. This position relationship causes the light spot to move at both end portions of the electrophoresis unit section 5 at a speed faster than in the vicinity of the central portion thereof (X−0), for example, when the vibrating mirror 22 is driven by the mirror driver 30 so as to vibrate at an isometric speed. This causes a difference in sensitivity of fluorescence detection between the central portion of the sample of the electrophoresis unit section 5 and its end portion. Hence, in this embodiment, the speed of driving the vibrating mirror 22 is corrected in order to move the spot light of the laser beams at an equal speed on the gel member of the electrophoresis unit section 5. In other words, the relationship between the position X of the spot light and the angle $\theta$ of the vibrating mirror 22 is set as shown in FIG. 5.

The angle $\theta$ of the vibrating mirror 22 is represented by the following:

$$\theta = \arctan(X/Z)$$

where
X is the distance in the plane direction having as an origin, a point from which a phantom line extends vertical to the surface of the gel member of the electrophoresis unit section from the center of rotation of the vibrating mirror 22; and Z is the distance from the center of rotation of the vibrating mirror 22 to the gel member of the electrophoresis unit section 5.

The angle of rotation and the distance of travel for the light scanning mechanism of this type may be corrected by an $f\theta$ lens; however, the $f\theta$ lens is expensive and the unit for mounting the $f\theta$ lens becomes heavy as a whole. In this embodiment, the mirror driver 30 is provided with a control circuit for implementing variable control of the speed of rotating the vibrating mirror 22 to control the speed of driving the rotation of the vibrating mirror 22 of the light scanning mechanism and the distance of moving the vibrating mirror 22 thereof, thereby correcting the angle of rotating the vibrating mirror 22 thereof.

Figure 6:
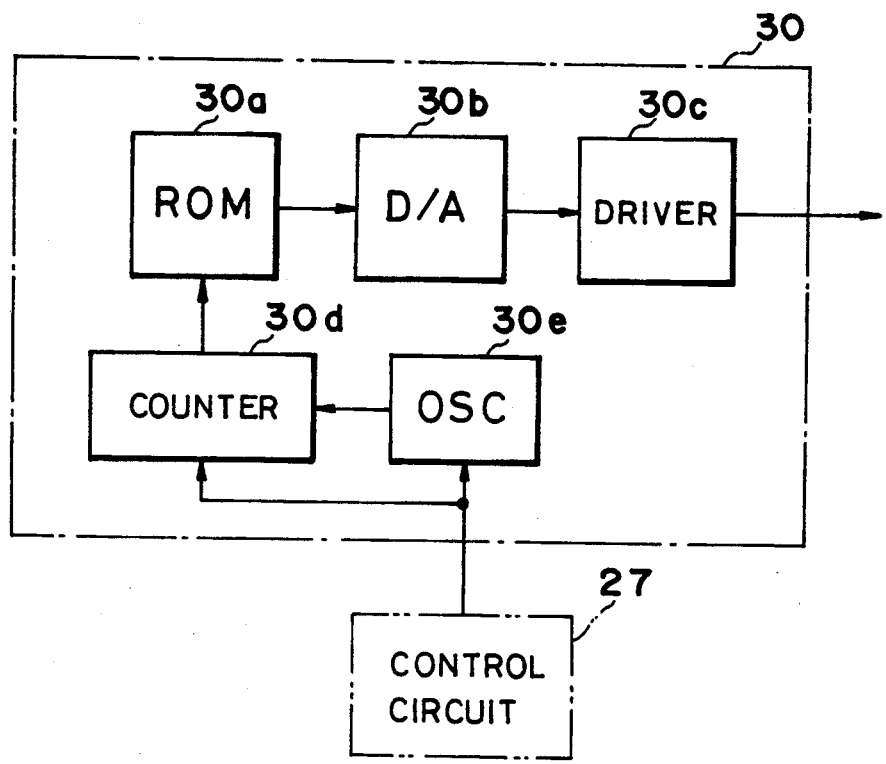
FIG. 6 is a block diagram showing the configuration of the essential portion of the control circuit for controlling a mirror driver for controlling the rotation of the vibrating mirror.

FIG. 6 is a block diagram showing the configuration of the essential portion of the circuit for controlling a mirror driver for controlling the rotation of the vibrating mirror 22.

A linear motor is employed as an actuator for the vibrating mirror 22, and the angle of rotating the vibrating mirror 22 can be controlled by applying voltage in proportion to the angle of rotation. In order to allow the spot lights of the laser beams to move at equal speeds on the surface of the gel member, the distance X of the surface thereof is so set as to become proportional to the time t. As the relationship between the angle $\theta$ of rotating the vibrating mirror and the distance X of moving the spot lights becomes as shown in FIG. 5, there is generated a signal in a wave form indicative of voltage corresponding to the graph of FIG. 5, wherein the axis of abscissas indicates the time, and the axis of ordinates indicates the voltage, and this signal controls the driving of the vibrating mirror 22. The generation of the control signal is controlled by the control circuit of the mirror driver 30, and the control signal is fed to the actuator of the vibrating mirror 22 for controlling the driving of the vibrating mirror 22.

As shown in FIG. 6, the mirror driver 30 comprises a read-only memory 30a having functional wave forms stored therein, a digital-analog conversion circuit 30b for converting the read function data into voltage signals, a driver 30c for amplifying the converted voltage signals and generating a control signal for controlling the driving of the mirror driver 30, a counter 30d for giving read addresses in time series to the memory 30a, and an oscillating circuit 30e for providing the counter with clock signals.

The oscillating circuit 30e is operated by an instruction from the control circuit 27 of the instrumentation unit body 7, and clock signals are entered into the counter 30d from the oscillating circuit 30e, thereby counting the clock signals and generating the read addresses to be fed to the read-only memory 30a in time series. As the read addresses generated by the counter 30d are fed to the read-only memory 30a the function data stored in advance are read out one after another from the read-only memory 30a. The function data (as shown in FIG. 5) relating to the angle of rotation of the vibrating mirror 22, are written in advance in the read-only memory and such function data are read in time series. In this example, the number of bits of the function data is 12 bits, and the function data to be read out are converted by the digital-analog conversion circuit 30b into analog voltage signals of for controlling the angle of rotation of the vibrating mirror 22. The voltage signals are processed to remove noises by filtering with the mirror driver 30. After the voltage signals are then amplified, they are fed to the vibrating mirror 22, thereby allowing the vibrating mirror 22 to be rotated at a desired angular speed so that the speed of moving (scanning) the spot lights of the laser beams on the electrophoresis unit section is constant.

The scanning speed is so set as to be variable at 0.5 Hz, 1 Hz, 5 Hz, 10 Hz, 20 Hz, 50 Hz, 100 Hz and 200 Hz in order to achieve an approximately logarithmically content slope for the FIG. 5C. This arrangement permits efficient reading by changing the reading speeds in accordance with the quantity of the fluorescent substances for use in labelling the samples for electrophoresis or the difference in the quantum efficiency of the fluorescent substances. The scanning speed can be designated through the operation display panel 7b or the data processor 8 by transmitting designation data from the control circuit 27 to the mirror driver 30, and controlling the counter 30d and the oscillating circuit 30e, thereby driving the vibrating mirror 22 at a desired scanning speed.

By implementing the control of driving the vibrating mirror 22 in the way as described hereinabove, the laser beams from the light source 21 are scanned and radiated as spot lights capable of moving on the electrophoresis unit section 5 at a constant speed. The irradiation of the gel member of the electrophoresis unit section 5 with the laser light excites the fluorescent substance present in the gel member thereof, thereby emitting fluorescence as indicated by 13.

Figure 7:
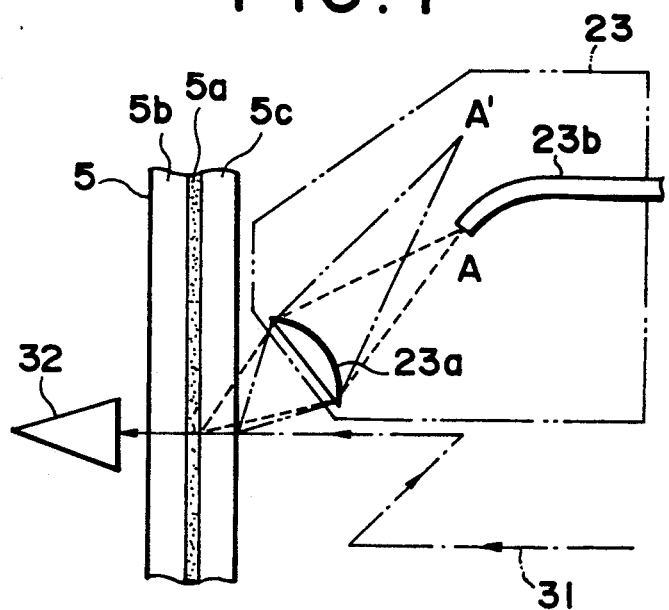
FIG. 7 is a schematic representation of the optical system in a light collector.
Figure 8:
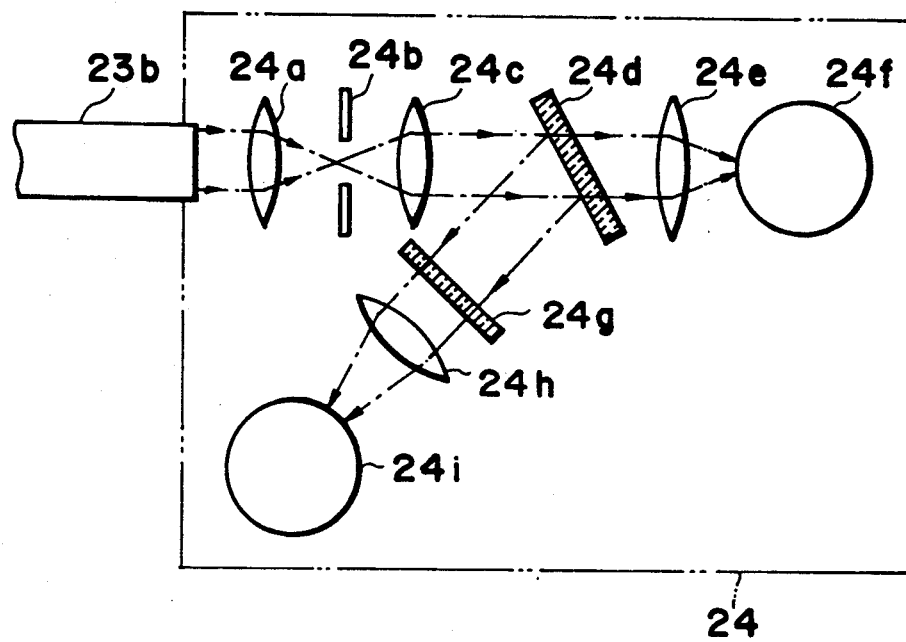
FIG. 8 is a schematic representation of the optical system in the optoelectric conversion section.

FIG. 7 is a schematic representation showing the detail configuration of the optic system in the light collector 13 for receiving the light generated from the gel member, and FIG. 8 is a schematic representation showing an example of the detail configuration of the optoelectric conversion section, particularly the light path. The gel member of the electrophoresis unit section 5 is interposed between the gel support members 5b and 5c, and each of the gel support members 5b and 5c is composed of boron silicate glass plates having a relatively lower magnitude of fluorescence in this embodiment, although quartz glass plates or various optical glasses can also be employed as the gel support members 5b and 5c.

As shown in FIG. 7, as the electrophoresis unit section 5 is irradiated with laser beams 31 which moves while being scanned, the light of the laser beams 31 is thrown on the gel support member 5c and transmits through the gel support member 5c in the direction of its thickness, reaching the gel member 5a through which in turn the irradiated light of the laser beams 31 advances in the direction of its thickness and the light transmits through the gel member 5a and then the gel member 5b. Each of the gel support members 5b and 5c is approximately 5 mm thick, and the gel member 5a is approximately 0.35 mm thick. The light of the laser beams 31 thrown on the gel support members 5b and 5c as well as the gel member 5a is so set as to reach the gel member 5a at a substantially equal light intensity in any position of the electrophoresis unit section 5. Further, the expansion of laser beams 31 or the reduction in their intensity due to scattered light to be generated on the plane of incidence of the irradiating light for the gel member 5a as well as the gel support members 5b and 5c can be decreased to a remarkable extent because their radiating light is incident in the direction perpendicular to the plane in the direction of thickness. Furthermore the laser beams 31 are damped by the optical trap 32 after transmission through the gel member, in order to cause no adverse influence as stray light.

The fluorescence is generated from the inside of the gel member 5a by scanning the exciting light in the manner as described hereinabove, and the fluorescence is collected by the light collector 23, together with scattered light by the exciting light. The scattered light generated in the gel support members 5b and 5c is separated in a geometrical-optical way by the spatial position relationship of the light path for receiving the light, thereby extracting only the fluorescence from the gel member and transmitting it to the optoelectrical conversion section 24. In the optoelectrical conversion section 24, the fluorescence and the scattered light generated in the gel member are separated from each other by the optical filter, and only the fluorescence separated from the gel member is transmitted to the optoelectrical conversion section 24 which can convert faint fluorescence into electrical signals by a photomultiplier.

Description will now be made of the configuration of the optical system in the light collector 23 and the optoelectrical conversion section 24 with reference to FIGS. 7 and 8.

As shown in FIG. 7, the light collector 23 is so arranged as to collect the fluorescence resulting from the electrophoresis unit section 5 and scattered light of the irradiating light resulting from the gel support members 5b and 5c by means of a cylindrical lens 23a. The scattered light and fluorescence from the electrophoresis unit section 5, which were received by the cylindrical lens 23a, are formed as images on the side opposite to the cylindrical lens 23a. In FIG. 7, the point A is a focal point of the fluorescence resulting from the gel member 5a and of the scatter light of the exciting light generated from the gel member 5a. On the other hand, for example, the scatter light of the exciting light generated on the surface of the gel support member 5c can form an image at the focal point A′. It is to be noted herein that the fluorescence can be separated from the scattered light resulting from the gel support members in a geometrical-optical manner due to the spatial position relationship of the light path for receiving the light by disposing the optical fiber array 23b at the focal point A so as to receive the fluorescence from the gel member 5a.

In the method for irradiating the gel member with the irradiating light in the direction of thickness of the gel member, a quantity of scattered light emitted in the boundary surfaces becomes very small because the refractive index of the gel member is approximately as low as 1.4 to 1.5 and relatively close to the refractive index of the gel support members, such as glass plates, and the gel member is closely attached to the gel support members to thereby form a tight boundary surface between them. Hence, the light received at the point A contains a lesser quantity of the scattered light of the exciting light emitting from the surface of the gel member 5a, while it contains a larger rate of fluorescence emitting from the inside of the gel member 5a.

When the irradiating light is scanned directly on the gel member 5a from which either one of, or both of, the gel support members 5b and 5c is or are removed, the scattered light may emit from the surface of the gel member in and quantity nearly equal to the quantity emitting from the surface of the glass plate panel as the gel support member. In this case, the glass plate of the reading table (7c in FIG. 3) of the instrumentation unit body 7 demonstrates substantially the same effect as the glass plate panel of the gel support member, thereby suppressing a detecting sensitivity from reducing to a great extent, and permitting the fluorescence emitting from the surface of the gel member to be detected with high efficiency. It is to be noted herein that, if the removal of the gel support members 5b and 5c is not particularly required at this moment of time in order to process the gel member 5a with a pigment or the like, it is preferred to read the gel member 5a in such a state that the gel member 5a is interposed between the gel support members 5b and 5c, thereby improving the signal-to-noise ratio.

Although one cylindrical lens is employed for the light collector 23 in this embodiment, another cylindrical lens may be disposed at the position symmetrical to the surface on which the laser beams are scanning or on the side opposite to the sample side. Further, when a magnitude of the fluorescence is insufficient, for example, cylindrical lenses and optic fiber arrays may be disposed at four locations so as to encircle the scanning line of the gel member emitting fluorescence, thereby increasing the quantity of light to be collected and enhancing the magnitude of fluorescence to be detected. In this case, it is effective to deviate the optic axes so as to cause no reflection from the surface of the cylindrical lens to adversely affect the cylindrical lens facing the other one. The fluorescence collected by the optical fiber array 23b is led to each of the optical fibers of the optic fiber arrays 23b, and the optical fibers are combined and entered into the optoelectric conversion section 24.

As shown in FIG. 8, the configuration of the optical system in the optoelectric conversion section 24 is arranged in such a way that the fluorescence entered into the optoelectric conversion section 24 from the optic fiber array 23b is so processed as to extract parallel light components only by a first lens 24a, a diaphragm 24b and a second lens 24c and the parallel light components are entered into the optical filter 24d, which in turn is disposed at an angle of approximately 20 degrees relative to the direction perpendicular to the direction of passage of the light. The optical filter 24d is so designed as to have a band pass filter characteristic having a central wavelength of 605 nm for the transmitting light and, further, a characteristic of reflecting the light having the wavelength of other than the transmitting light, which reflects on the side of entering into the optical filter 24d. Hence, the wavelength component of fluorescence from a first fluorescent substance can be extracted from the light that has transmitted through the optic filter 24d.

The wavelength component of the fluorescence is then collected by a third lens 24e and led to a first photomultiplier 24f where electrical signals are produced for the intensity of fluorescence of the first wavelength component of the fluorescence. Likewise, the fluorescence having the wavelength components of second and following fluorescent substances can be extracted from the light reflecting from the optical filter 24d. Hence, as in the embodiment as shown in FIG. 8, the light reflected from the optical filter 24d is further led to a second optic filter 24g, which in turn removes the wavelength component of the exciting light, followed by collecting light with a fourth lens 24h and generating electrical signals corresponding to the intensity of fluorescence of the wavelength of the second fluorescence through a second photomultiplier 24i.

Figure 9:
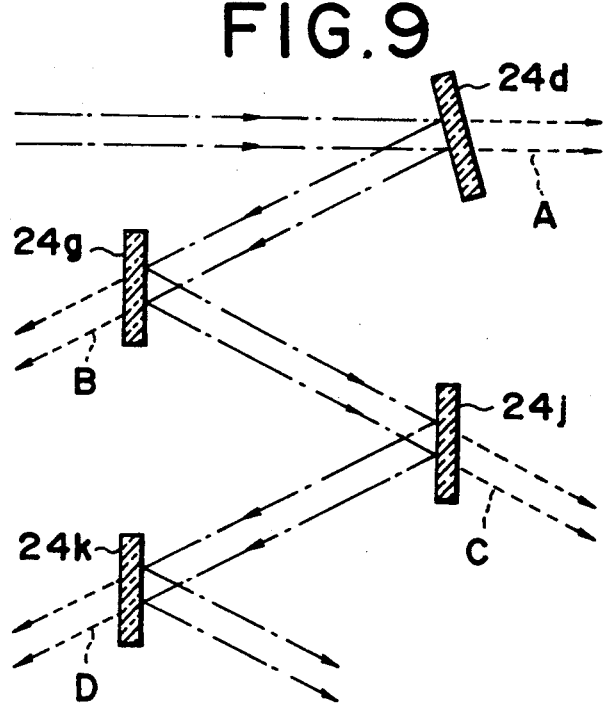
FIG. 9 is a schematic representation showing another example of the optical system in the optoelectric conversion section.

FIG. 9 is a schematic representation showing another example of the detail configuration of the optical filter section for separating fluorescence into a number of wavelength components through a number of optical filters.

In separating the fluorescence into a number of wavelength components, the optical filter section is configured as in FIG. 9, in which the second optical filter 24g is disposed at the position at which the light reflects from the first optical filter 24d and a third optical filter 24j is disposed at the position at which the light reflects from the second optic filter 24g. Further a fourth optical filter 24k is disposed at the position at which the light reflects from the third optical filter 24j. This arrangement can separate fluorescence having different wavelength components as lights A, B, C and D transmitting through the first, second, third and fourth optical filters 24d, 24g, 24j and 24k, respectively.

By separating the resulting fluorescence from the scattered light of the exciting light, the respective photomultipliers 24f and 24i generate the electrical signals corresponding to the intensity of fluorescence in accordance with the wavelength components of each fluorescence with the improved signal-to-noise ratio. The resulting electrical signals are entered into the amplifiers of plural systems, each system of which amplifies faint signals to a sufficient extent in an amplification stage containing an integral circuit.

Figure 10:
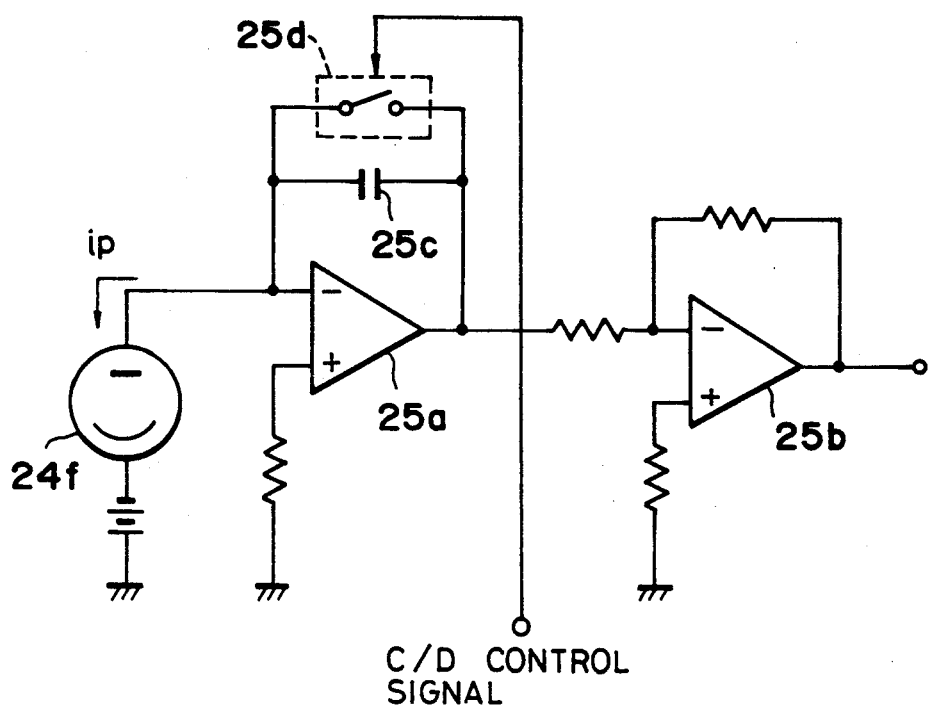
FIG. 10 is a circuit diagram showing the circuit configuration of an amplifier containing an integral circuit.

FIG. 10 is a circuit diagram showing the circuit configuration of an amplifier containing the integral circuit. As shown in FIG. 10, the amplifier 25 has an integral circuit composed of an operational amplifier in the front amplification stage and an output amplification circuit composed of an operational amplifier in the following amplification stage. The electrical signals from the photomultiplier 24f are entered into an operational amplifier 25a which in turn constitutes the integral circuit, together with a condenser 25c and a switch 25d for controlling the integral operation. The output of the integral circuit is entered into an operational amplifier 25b and amplified with a gain to be determined by an external resistance, followed by transmission to an analog-digital converting circuit which follows.

Figure 11:
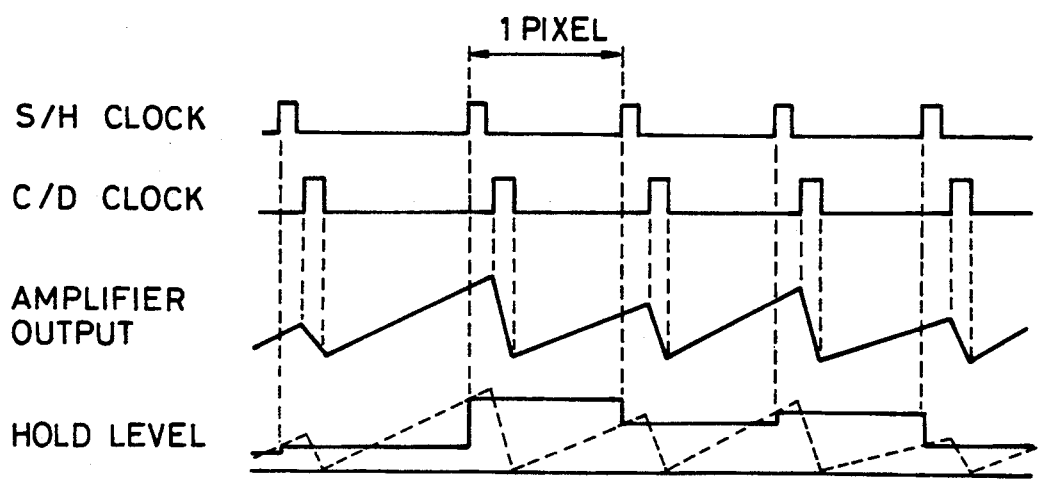
FIG. 11 is a time chart showing the timing of reading operations by the amplifier.

The operation in the amplifier 25 containing the integrating circuit having the configuration as described hereinabove will now be described with reference to the timing chart as shown in FIG. 11. The output of the photomultiplier 24f has a very large output impedance so that it can be regarded as if it were a source of electric current. For the operational amplifier 25a, there is employed a high-input impedance of a FET (Field Effective Transistor) input type. Hence, when the switch 25d is turned off, the output current ip of the photomultiplier 24f flows entirely as it is through the condenser 25c. The output voltage of the operational amplifier 25a is converted into an output of a ramp function type, as shown in FIG. 11. Such integrating operations involve, integrating for a period of time corresponding to one pixel, allowing a sampling circuit within the analog-digital conversion circuit 26 to sample signals at a timing matched with a S/H clock, holding the resulting signals and, supplying the analog signals to the analog-digital converting circuit 26 where the analog signals are converted into digital signals. After the signals are held, the C/D clock serving as a C/D control signal to be added to the switch 25d is made active, thereby discharging electrical charges accumulated in the condenser 25c. The operations are repeated in the way as described hereinabove.

The amplification stage using the operational amplifier integrating circuit can be a pseudo-integrating circuit composed of a resistance and a condenser only. It is to be noted, however, that the integrating circuit in the operational amplifier having the configuration as described hereinabove can provide a higher signal-to-noise ratio because it can integrate the electrical charges of the electrical signals from the photomultiplier 24f to an almost complete level. Further, the integrating time can be changed in an arbitrary manner by changing the C/D clock of the C/D control signals for the switch 25d. Hence, a degree of amplification for amplifying faint signals in a comprehensive fashion can readily be adjusted. In this embodiment, the control can be carried out so as to agree with an area of the reading sample by corresponding to or synchronizing with the operation of the mirror driver 30 as shown in FIG. 4, thereby saving time by avoiding useless reading periods.

Further, the speed of scanning the exciting light and the integrating time of the amplifier on the side of the receiving light can be set so as to agree with the intensity of fluorescence from the sample with high freedom, thereby permitting a very flexible device configuration. Furthermore, when the integral operations are to be implemented with the condenser and the resistance only, the values of the condenser and the resistance can be shifted so as to define a time constant corresponding to the speed of scanning the irradiating light, so that the integrating operation can be realized in a pseudo fashion.

The electrical signals amplified by the amplifier 25 (FIG. 2) are entered into the analog-digital conversion circuit 26, where the analog signals are converted into digital signals. The signals indicative of the fluorescence detected, which are converted into digital data, are stored in the memory 28 and the data stored in the memory 28 are transmitted to the data processor 8 through an interface circuit 29. The overall control for performing such signal processing is carried out by the control circuit 27.

Description will now be made of a variant example of the elements structuring the multi-colored electrophoresis pattern reading apparatus according to the embodiment of the present invention.

Figure 12:
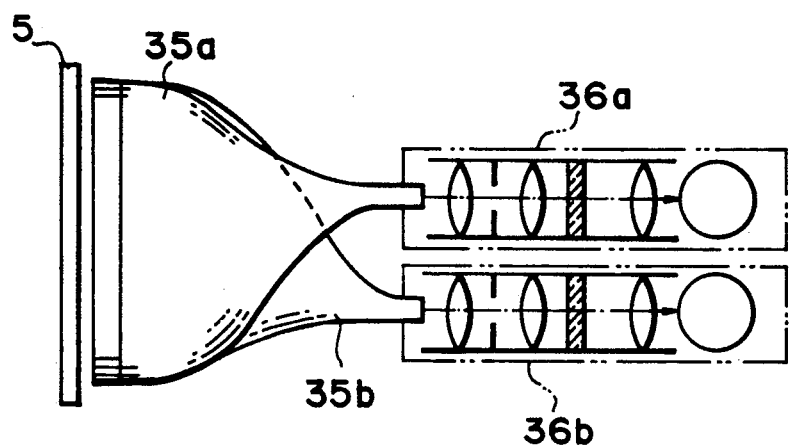
FIG. 12 is a schematic representation showing another example of the configuration of the light collector for detecting plural separated wavelength components of fluorescence, and the optoelectric conversion section.

FIG. 12 is a schematic representation showing another example of the configuration of the light collector for detecting plurally separated wavelength components of fluorescence and the optoelectric conversion section.

In the previous embodiment, the configuration for separating a plurality of wavelength components of fluorescence is implemented by employing a plurality of optical filters for the optoelectric conversion unit 24. It can further be noted that the fluorescence intensity of each of the desired fluorescent wavelength components can be detected by each of the optical filters by employing a plurality of systems consisting of the light collectors and the optoelectric conversion units. In this case, the wavelength components of fluorescence can be individually detected by the optic system of each of the light collectors and the optoelectric conversion units, so that even faint fluorescence can be detected with high sensitivity.

As shown in FIG. 12, this configuration provides electrical signals of each of the wavelength components of fluorescence by dividing the fluorescence entering from the electrophoresis unit section 5 with the optical fiber arrays 35a and 35b of the plural light collectors so as to be distributed uniformly in the position in which each fluorescence enters, and then by supplying the fluorescence collected by each of the optical fiber arrays 35a and 35b to each of the optoelectric conversion units 36a and 36b. A set of the optical fiber arrays 35a and 35b may further be disposed, thereby allowing the fluorescence to be divided into different wavelength components of the fluorescence. In this case, however, photons of each fluorescence component so divided are reduced in number. The characteristic of this configuration resides in the fact that, as the wavelength components of the fluorescence can be detected individually by the optical systems of each of the light collectors and the optoelectric conversion units, the wavelength of fluorescence to be detected can be changed individually and with freedom. Further, reliability can be improved, for instance, when there is employed a duplicate system for receiving the light of the identical wavelength.

Figure 13:
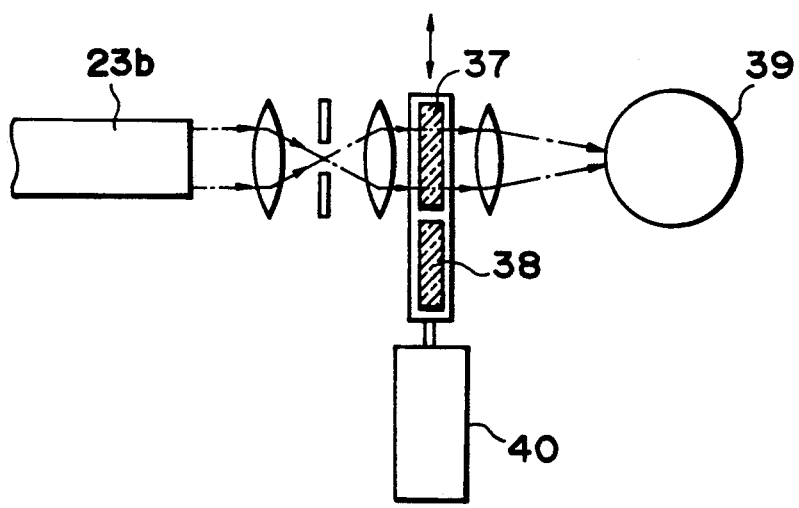
FIG. 13 is a schematic representation showing an example of the configuration of the optoelectric conversion section to be employed when an optical filter is mechanically moved to change the wavelength component of fluorescence to be selected.

FIG. 13 is a schematic representation showing an example of the configuration of the optoelectric conversion section to be employed when the optical filter is mechanically moved to change the wavelength component of fluorescence to be selected. The fluorescence entered from the optical fiber array 23b is so processed as to collimate the parallel components only through the first lens, the diaphragm and the second lens, and the parallel components of the fluorescence are then allowed to reach the photomultiplier 39 through the optical filter 37 or the optical filter 38. The optical filter 37 or 38 may be shifted so as to be selected in accordance with requirements by using an electromagnetically reciprocating solenoid 40. This arrangement allows a time sharing separation of the wavelength components of the fluorescence by shifting the plural optical filters in a time sharing way. This arrangement requires only one photomultiplier 39, which is very expensive, to separate the wavelength components of fluorescence in a time sharing fashion, so that costs of the device configuration can be reduced.

Figure 14:
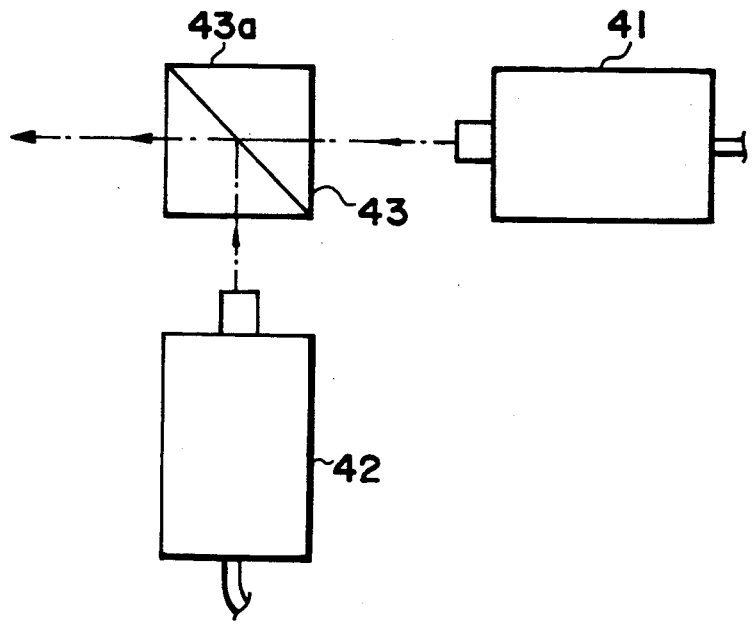
FIG. 14 is a schematic representation showing an example of the configuration of the light source in which plural kinds of light beams having different wavelengths are united into one beam.

FIG. 14 is a schematic representation showing an example of the configuration of the light source in which plural kinds of excited light having different wavelengths are united into one beam. In this configuration, the laser beams generated from each of a first light source 41 and a second light source 42, each emitting light having a predetermined wavelength component, are entered into a cube-shaped beam splitter 43. In this embodiment, the light sources comprise the first light source 41 for emitting green laser beams having a wavelength of 532 nm and the second light source 42 for emitting argon ion laser beams. The surface 43a of a half mirror disposed in the beam splitter 43 has a membrane capable of transmitting the light from the first light source 41 while reflecting the light from the second light source 42. This arrangement permits the light beams from the two light sources to be employed as one separate light beam.

It is to be noted that the kinds of the fluorescent substances to be employed for labelling the samples can be increased by employing a plurality of light sources for emitting exciting light for exciting the fluorescent substances contained in the electrophoresis pattern. In this embodiment, fluorescent substances such as Texas red, tetramethyl rhodamin isothiocyanate (TRITC) and so on can be excited by the light from the first light source 41, while fluorescent substances such as fluorescein isothiocyanate, 4-chloro-7-nitrobenz-2-oxa-1-diazole (NBD chloride) and so on can be excited by the light from the second light source 42.

In the embodiment of the configuration of the light source as described hereinabove, one beam splitter is employed as a structuring element for the light source. It is to be noted, however, that two beam splitters may be employed by disposing the second beam splitter on the side of the beam united by the first beam splitter, thereby allowing two or more light beams to be admixed with each other and united into one beam. Further, it is to be noted that a laser having a plurality of oscillating wavelengths and a laser capable of emitting higher harmonics may be employed as a light source.

Figure 15:
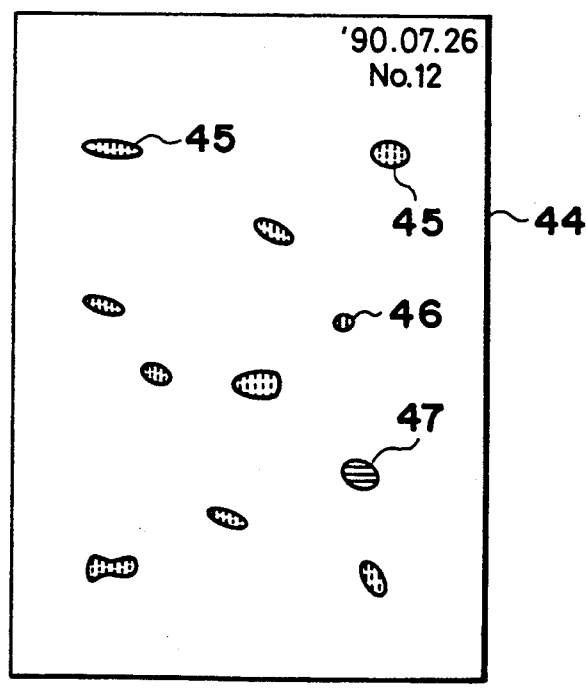
FIG. 15 is a schematic representation showing an example of output of an electrophoresis pattern obtained by reading the results of two-dimensional electrophoresis of a protein sample with the multi-colored electrophoresis pattern reading apparatus.
Figure 16:
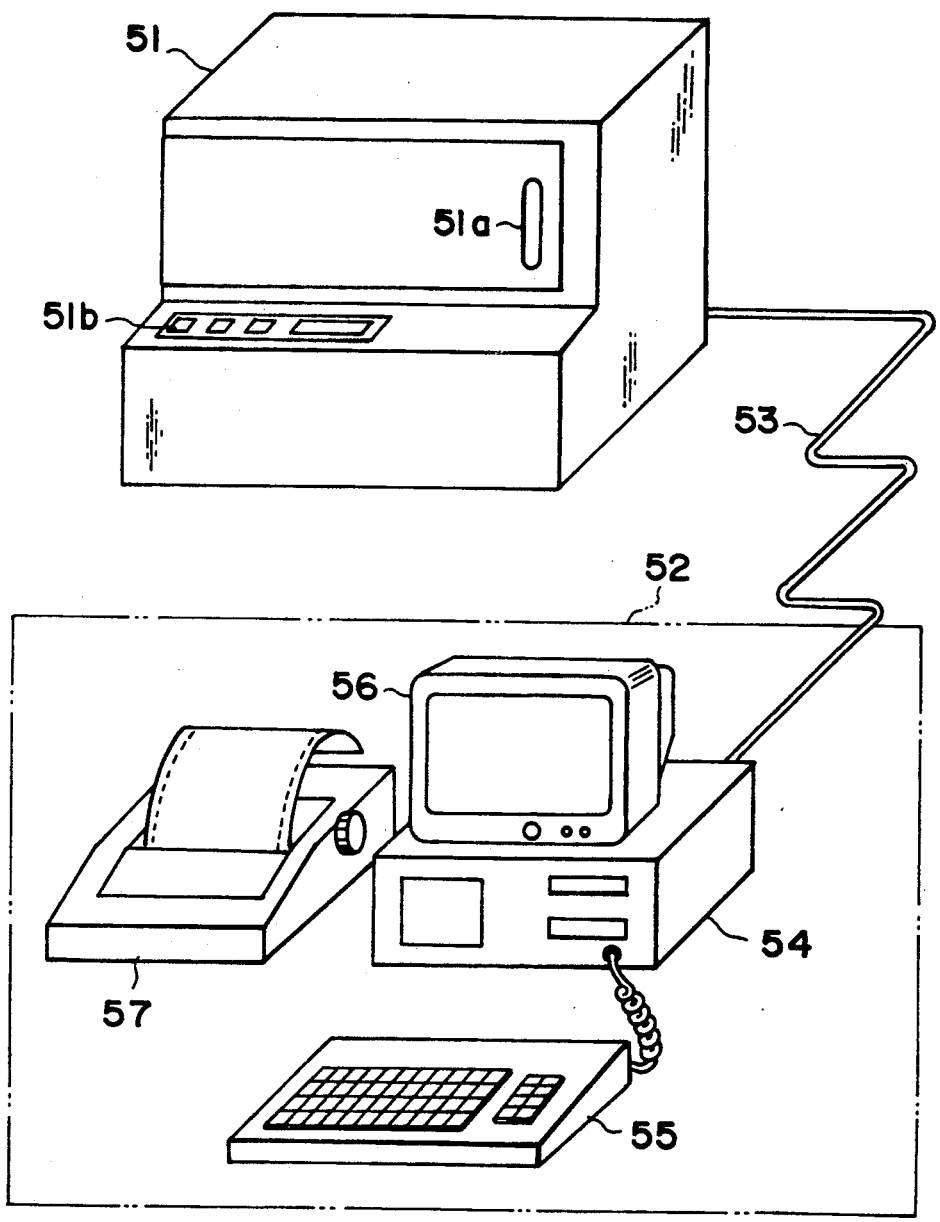
FIG. 16 is a perspective view showing a conventional electrophoresis apparatus of a fluorescent type.
Figure 17:
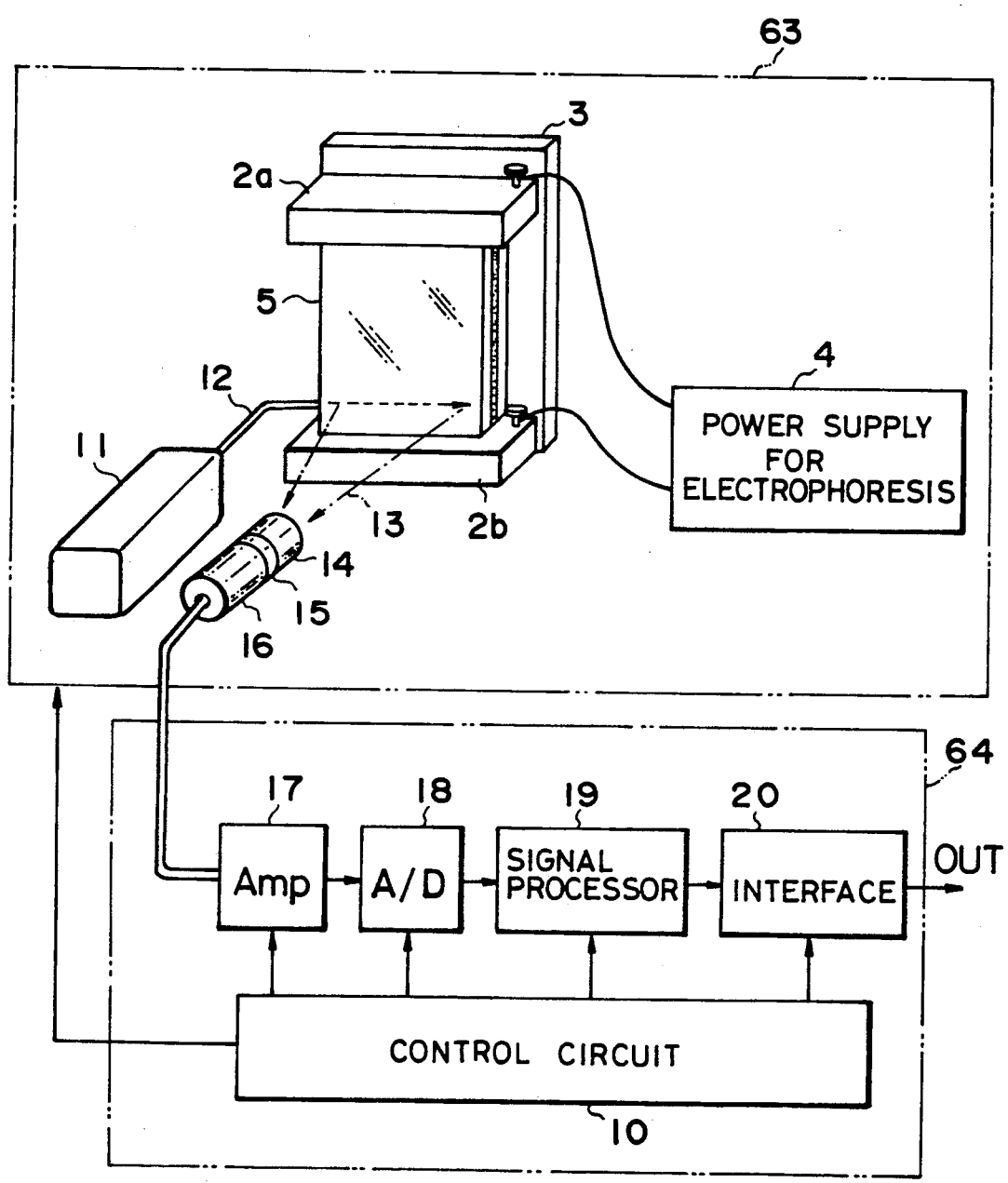
FIG. 17 is a block diagram showing the configuration of the inside of the electrophoresis and instrumentation unit of the conventional electrophoresis pattern reading apparatus.

FIG. 15 is a schematic representation showing an example of an output of an electrophoresis pattern obtained by reading the results of electrophoresing a sample of a protein with the multi-colored electrophoresis pattern reading apparatus in a two-dimensional way. In this embodiment, for instance, the data on the electrophoresis pattern read from a reference sample is colored red and the data on the electrophoresis pattern read from a sample to be detected is colored blue. It is noted as a matter of course that any combination of colors can be employed.

The example as shown in FIG. 15 reveals that bands identified by 45 on the electrophoresis pattern are colored violet, as indicated by vertical dot lines in the drawing, and the bands 45 represent a combination of the band in red resulting from the reference sample and the band in blue resulting from the sample to be detected, each of the bands being located in the identical positions on the electrophoresis pattern. This means that the sample to be detected contains the same structural fragment portion as the reference sample.

When the samples have different structural fragment portions, the bands resulting from that fragment portions, as indicated by 46 and 47 in the drawing, are located in different positions on the electrophoresis pattern, and are colored red and blue, which originate from the reference sample and the sample to be detected, respectively. This electrophoresis pattern can serve to a great extent as a ready and simple comparison among the bands simply by determining the colors on the bands.

Further, experimental items such as experiment date, experiment number, conditions, etc. should be written with oil-base ink or the like for managing the image from X-ray films. On the other hand, they can be written together with the output of the electrophoresis pattern for the apparatus according to the present invention merely by entering those experimental items at predetermined positions through an input unit. This permits the output electrophoresis patterns to be managed with ready reference and easy availability.

As described hereinabove, the multi-colored electrophoresis pattern reading apparatus according to the present invention allows an electrophoresis plate itself (the electrophoresis unit section) to be read as it is after electrophoresis has been finished and mounted to the reading unit separately disposed from the electrophoresis unit, so that even if a long period of time is required, as for the case in which two-dimensional electrophoresis results are to be read, the electrophoresis unit can be employed for electrophoresing another sample, thereby improving operational efficiency of the electrophoresis unit to a great extent.

Further, as described hereinabove, the multi-colored electrophoresis pattern reading apparatus according to the present invention can read a plurality of fluorescent pigments labelled on the samples by separating the light components by their wavelengths, thereby permitting the electrophoresis results to be obtained from two or more different samples at the same time. Furthermore, the multi-colored electrophoresis pattern reading apparatus of the present invention is so arranged as to cause a deviation such as a warp resulting from electrophoresis to occur on the samples in the same manner, so that the molecular weights of the two or more samples and other parameters, can be compared without correction of the electrophoresis results, thereby making a comparison of the electrophoresis results very simple and easy. In addition, the gel member is removed from the electrophoresis unit and mounted to the reading unit after the electrophoresis has been finished, so that the results obtainable by two-dimensional electrophoresis as well as by one-dimensional electrophoresis can be read in the same manner.

What is claimed is:

1. A multi-colored electrophoresis pattern reading apparatus for labelling each of plural samples separately with each of plural fluorescent substances respectively having different fluorescence wavelengths, subjecting the plural samples to electrophoresis with a gel to develop an electrophoresis pattern, exciting the fluorescent substances labelled on the respective plural samples of the developed electrophoresis pattern to emit fluorescence, and reading a fluorescent pattern emitting the fluorescence, comprising:
   a light source means for irradiating the developed electrophoresis pattern with irradiating light for exciting the fluorescent substance labelled on the sample;
   a light scanning means for scanning the irradiating light to irradiate the gel in the direction of thickness of the gel with the irradiating light from the light source means;
   a light receiving means for receiving the fluorescence, separated from scattered light resulting from a reading surface, on the basis of a spatial position relationship of a light receiving path, including a light receiving surface located in a direction different from an optical axis of the irradiating light;
   an optical filter means for separating optical signals received by the light receiving means into plural fluorescence wavelengths;
   an optoelectric conversion means for generating electrical signals by subjecting the optical signals separated by the optical filter means to optoelectric conversion; and
   an amplifier means for amplifying the electrical signals form the optoelectric conversion means by an integrating operation corresponding to scanning of the irradiating light, and for generating electrical signals indicative of fluorescence from the developed electrophoresis pattern one after another.

2. A multi-colored electrophoresis pattern reading apparatus as claimed in claim 1, wherein the optical filter means divides the optical signals transmitted from the light receiving means into at least two divided optical signals; and wherein each of the divided optical signals is wavelength-separated by an optical filter having a predetermined wavelength.

3. A multi-colored electrophoresis pattern reading apparatus as claimed in claim 1, wherein the optical filter means separates the optical signals transmitted from the light receiving means by wavelength by using an optical filter having a wavelength for reflecting light different from a wavelength for light to be transmitted.

4. A multi-colored electrophoresis pattern reading apparatus as claimed in claim 1, wherein the optical filter means separates by wavelength by shifting a plurality of optical filters and changing a wavelength to be separated in a time sharing way.

5. A multi-colored electrophoresis pattern reading apparatus as claimed in claim 1, further comprising a printing means for printing multiple colors; wherein optical signals received by the light receiving means are separated into plural wavelengths, and electrical signals converted from the optical signals by the optoelectric conversion means, and corresponding to the plural separated wavelengths, are provided to the printing means for printing as a colored electrophoresis pattern.

6. A multi-colored electrophoresis pattern reading apparatus for labelling plural samples separately with at least one fluorescent substance, subjecting the plural samples to electrophoresis with a gel to develop an electrophoresis pattern, exciting the fluorescent substance or substances labelled on the respective plural samples of the developed electrophoresis pattern to emit fluorescence, and reading a fluorescent pattern emitting the fluorescence, comprising:

a light source means for irradiating the developed electrophoresis pattern with irradiating light for exciting the fluorescent substance labelled on the sample;

a light scanning means for scanning the irradiating light from the light source to irradiate the gel in the direction of thickness of the gel with the irradiating light;

a light receiving means having at least one light receiving surface for receiving fluorescence resulting from the developed electrophoresis pattern, separated from scattered light resulting from a reading surface, on the basis of a spatial position relationship of a light receiving path, by setting at least one of said light receiving surfaces in a direction different from an optical axis of the irradiating light;

an optical filter means for separating optical signals received by the light receiving means into plural wavelengths of the fluorescence;

an optoelectric conversion means for subjecting optical signals separated by the optical filter means to optoelectric conversion to thereby generate electrical signals; and an amplifier means for amplifying the electrical signals from the optoelectric conversion means by an integrating operation corresponding to scanning of the irradiating light, and for generating electrical signals indicative of fluorescence from the developed electrophoresis pattern one after another.

7. A multi-colored electrophoresis pattern reading apparatus as claimed in claim 6, wherein the light source means includes a plurality of light sources for exciting the fluorescent substance or substances with light beams having a plurality of wavelengths, the fluorescent substance or substances of the developed electrophoresis pattern are irradiated in a time sharing way, and each light source provides exciting light having a different wavelength.

8. A multi-colored electrophoresis pattern reading apparatus as claimed in claim 6, further comprising a printing means for printing multiple colors; wherein optical signals received by the light receiving means are separated into plural wavelengths, and electrical signals converted from the optical signals by the optoelectric conversion means, and corresponding to the plural separated wavelengths, are provided to the printing means for printing as a colored electrophoresis pattern.

* * * * *